(12) United States Patent
Walker et al.

(10) Patent No.: US 10,012,561 B2
(45) Date of Patent: Jul. 3, 2018

(54) INTEGRITY TESTING OF STORAGE TANK STRUCTURE USING ROBOTIC ULTRASOUND

(71) Applicant: Sonasearch, Inc., Redmond, WA (US)

(72) Inventors: Stephen Edward Walker, Redmond, WA (US); Sheldon Rubin, Redmond, WA (US)

(73) Assignee: Sonasearch, Inc., Redmond, WA (US)

( * ) Notice: Subject to any disclaimer, the term of this patent is extended or adjusted under 35 U.S.C. 154(b) by 54 days.

(21) Appl. No.: 14/924,567

(22) Filed: Oct. 27, 2015

(65) Prior Publication Data

US 2016/0299031 A1    Oct. 13, 2016

Related U.S. Application Data

(60) Provisional application No. 62/122,911, filed on Nov. 3, 2014.

(51) Int. Cl.
*G01N 29/265*    (2006.01)
*G01M 3/24*    (2006.01)
(Continued)

(52) U.S. Cl.
CPC ............ *G01M 3/24* (2013.01); *G01N 29/043* (2013.01); *G01N 29/0618* (2013.01); *G01N 29/262* (2013.01); *G01N 29/265* (2013.01); *G01N 2291/0258* (2013.01); *G01N 2291/02854* (2013.01)

(58) Field of Classification Search
CPC . G01M 3/005; G01N 29/043; G01N 29/0618; G01N 29/069; G01N 29/262; G01N 29/265; G01N 2291/0258; G01N 2291/02854; G01N 2291/0234; G01N 2291/106; G01N 2291/2636; G01N 2291/2638
USPC .......... 73/623, 625, 262, 628, 618, 633, 634, 73/641, 602
See application file for complete search history.

(56) References Cited

U.S. PATENT DOCUMENTS 3,987,666 A * 10/1976 Blanc .................... B62D 55/265
                                                        180/6.48
4,569,230 A *  2/1986 Asty ..................... G21C 17/013
                                                        376/249
(Continued)

OTHER PUBLICATIONS

Bashor, C., "Reducing the Risk of Aboveground Storage Tank Floor Leaks," Minnesota Pollution Control Agency, Freshwater Spills Symposium, Cleveland, Ohio, Mar. 19-21, 2002, 67 pages.
(Continued)

*Primary Examiner* — Manish S Shah
*Assistant Examiner* — Rose M Miller
(74) *Attorney, Agent, or Firm* — Christensen O'Connor Johnson Kindness PLLC

(57) ABSTRACT

An objective of this invention is to provided apparatus and methods to test the integrity of empty and full tanks. Another object of this invention is to provide a granular inspection of the tank. Another object of this invention is to provide precision positioning information of sample points. Another object of this invention is to provide automated inspection pattern and correction. Another object of this invention is to minimize hazardous working conditions.

18 Claims, 16 Drawing Sheets
(11 of 16 Drawing Sheet(s) Filed in Color)

(51) Int. Cl.
*G01N 29/04* (2006.01)
*G01N 29/06* (2006.01)
*G01N 29/26* (2006.01)

(56) References Cited

U.S. PATENT DOCUMENTS

| | | | |
|---|---|---|---|
| 5,047,990 A | 9/1991 | Gafos et al. | |
| 5,205,174 A | 4/1993 | Silverman et al. | |
| 5,451,135 A | 9/1995 | Schempf et al. | |
| 5,942,687 A | 8/1999 | Simmonds et al. | |
| 6,104,970 A | 8/2000 | Schmidt, Jr. et al. | |
| 6,253,615 B1 | 7/2001 | Simmonds et al. | |
| 6,317,387 B1 | 11/2001 | D'Amaddio et al. | |
| 6,738,314 B1 | 5/2004 | Teeter et al. | |
| 6,838,614 B2 | 1/2005 | Silverman et al. | |
| 6,882,412 B2 | 4/2005 | Silverman et al. | |
| 7,017,432 B2 | 3/2006 | Silverman et al. | |
| 7,460,980 B2* | 12/2008 | Hinn | G01M 3/005 324/220 |
| 7,467,560 B2 | 12/2008 | Silverman et al. | |
| 7,743,660 B2* | 6/2010 | Marsh | G01N 29/223 73/633 |
| 7,900,517 B2* | 3/2011 | Chougrani | G01N 29/043 73/592 |
| 7,950,284 B2* | 5/2011 | Dijkstra | G01N 29/225 73/600 |
| 8,042,399 B2* | 10/2011 | Pasquali | G01N 29/225 73/622 |
| 8,521,453 B1 | 8/2013 | Silverman et al. | |
| 2003/0067249 A1* | 4/2003 | Lockwood | B06B 1/0622 310/324 |
| 2003/0136195 A1* | 7/2003 | Krieg | G01N 29/07 73/628 |
| 2007/0276552 A1* | 11/2007 | Rodocker | B62D 57/00 701/2 |
| 2010/0313665 A1* | 12/2010 | Chougrani | G01N 29/043 73/623 |
| 2012/0281096 A1 | 11/2012 | Gellaboina et al. | |
| 2013/0133429 A1* | 5/2013 | Palma | G01N 29/265 73/623 |
| 2013/0319120 A1* | 12/2013 | Fetzer | G01N 29/225 73/628 |
| 2014/0081504 A1 | 3/2014 | Smith et al. | |

OTHER PUBLICATIONS

Bondurant, P.D., "Tank Bottom Inspection System Notes" (from TechCorr Publications/Patent Review), Jun. 18, 2010, 4 pages.
"InTANK® Robotic Inspection Service," TechCorr USA, LLC, Pasadena, Texas, Jun. 4, 2010, 2 pages.
International Search Report dated Dec. 29, 2015, issued in corresponding International Application No. PCT/US2015/057675, filed Oct. 28, 2015, 2 pages.
Nance, T., "Tank 19F Folding Crawler Final Evaluation, Rev. 0," Westinghouse Savannah River Company, Aiken, S.C., Document No. WSRC-TR-2000-00301 Final, Nov. 3, 2000, 40 pages.
Opurum, P., et al., "Target Functional Specification: SR 325 Intrusively Deployed Active NDE (IDAN)," Chevron, Sep. 14, 2011, 6 pages.
Peters, T.J., et al., "Alternative Inspection Methods for Single Shell Tanks," Pacific Northwest National Laboratory and Battelle/U.S. Department of Energy, Document No. PNNL-19113, Jan. 2010, 43 pages.
"Petroleum, Project Fact Sheet: Robotics Inspection System for Storage Tanks," Fact Sheet No. DOE/GO-10099-7312, Solex Environmental Systems, Inc., Houston, Jan. 1999, 2 pages.
Shepard, R., "Electromagnetic Acoustical Transducer (EMAT) Inspection of Storage Tanks," 16th World Conference on NDT, Montreal, Aug. 30-Sep. 3, 2004, 3 pages.
Silverman, E.B., et al., "In-Service Oil Tank Cleaning and Inspection System: Results of Eight (8) Independent Validations," Proceedings of the 2000 ASNT Spring Conference and 9th Annual Research Symposium, Birmingham, Ala., Mar. 27-31, 2000, 9 pages.
Summa, V., "In-Service Above Ground Storage Tanks Inspection Robotics Technology Update," TechCorr Inspection and Engineering, LLC, Houston, Inspectioneering Journal, Mar./Apr. 2008, pp. 11-20.
"TechCorr USA, LLC Announces New Technology, the Sludge Profiler Service Line," TechCorr USA, LLC, Pasadena, Texas, Jul. 2009, 1 pages.
Understanding In-Service AST Inspection Robotics and Using Auxiliary Techniques: 2.0 History and Technology Background, TechCorr Inspection and Engineering, Pasadena, Texas, modified Dec. 7, 2011, <www.techcorr.com> [retrieved Oct. 31, 2016], 69 pages.

* cited by examiner

INTEGRITY TESTING OF STORAGE TANK STRUCTURE USING ROBOTIC ULTRASOUND

CROSS-REFERENCES TO RELATED APPLICATIONS

This application takes priority to provisional application No. 62/122,911 filed on Nov. 3, 2014 and incorporated herein, in its entirety, by reference.

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

Not Applicable

BACKGROUND

Storage tanks must be inspected periodically to determine whether a tank is in need of replacement or repair. Inspections detect corrosion, fissures, cracks, and other anomalies in tank walls and floors. Inspection techniques may include acoustic, electrical and/or mechanical techniques. Inspection reports usually contain basic measurements and an estimate of metal loss.

Tanks must be empty for inspection because testing personnel must have access to the inside of the tank. Consequently, inspecting fluid filled tank walls becomes expensive and dangerous. In most cases, tank operations in at least two tanks must stop so that fluid from the tank to be inspected can be pumped into a holding tank. The tank to be inspected may have to be cleaned before inspection personnel can enter the tank. Inspection personnel will, more likely than not, be required to wear personal protection equipment and carry oxygen to inspect tanks. Once inspection is completed, fluid must be pumped from the holding tank into the inspected tank.

FIG. 1 shows a typical tank used by refineries, storage facilities, and pipelines. Other tanks include, but are not limited to, tanks on super tankers, off shore oil production platforms, Floating Production Storage and Offloading vessels (FPSOs), airport storage tanks and oil-transport rail cars. Volatile petroleum products that may be stored in these types of tanks include flammable and combustible liquids and gases, and may produce flammable or combustible liquids, gases, vapors or mists when mixed with air under normal atmospheric conditions. The normal operating temperature range for this type of system is −20 C to +60 C at normal atmospheric pressures of 980 to 1050 millibars. Taking a typical tank out of operation, cleaning, and inspecting it can cost in the neighborhood of $5,000,000.

SUMMARY OF THE INVENTION

An objective of this invention is to provide an apparatus and method to test the integrity of empty and full tanks. Another object of this invention is to provide a granular inspection of the tank. Another object of this invention is to provide precision positioning information of sample points. Another object of this invention is to provide automated inspection pattern and correction. Another object of this invention is to minimize hazardous working conditions.

BRIEF DESCRIPTION OF THE DRAWINGS

The patent or application file contains at least one drawing executed in color. Copies of this patent or patent application publication with color drawings will be provided by the Office upon request and payment of the necessary fee.

Other features and advantages of the present invention will become apparent in the following detailed descriptions of the preferred embodiment with reference to the accompanying drawings, of which.

DETAILED DESCRIPTION OF THE INVENTION

Figure 1:
FIG. 1 is an environmental view of an exemplary tank.
Figure 2:
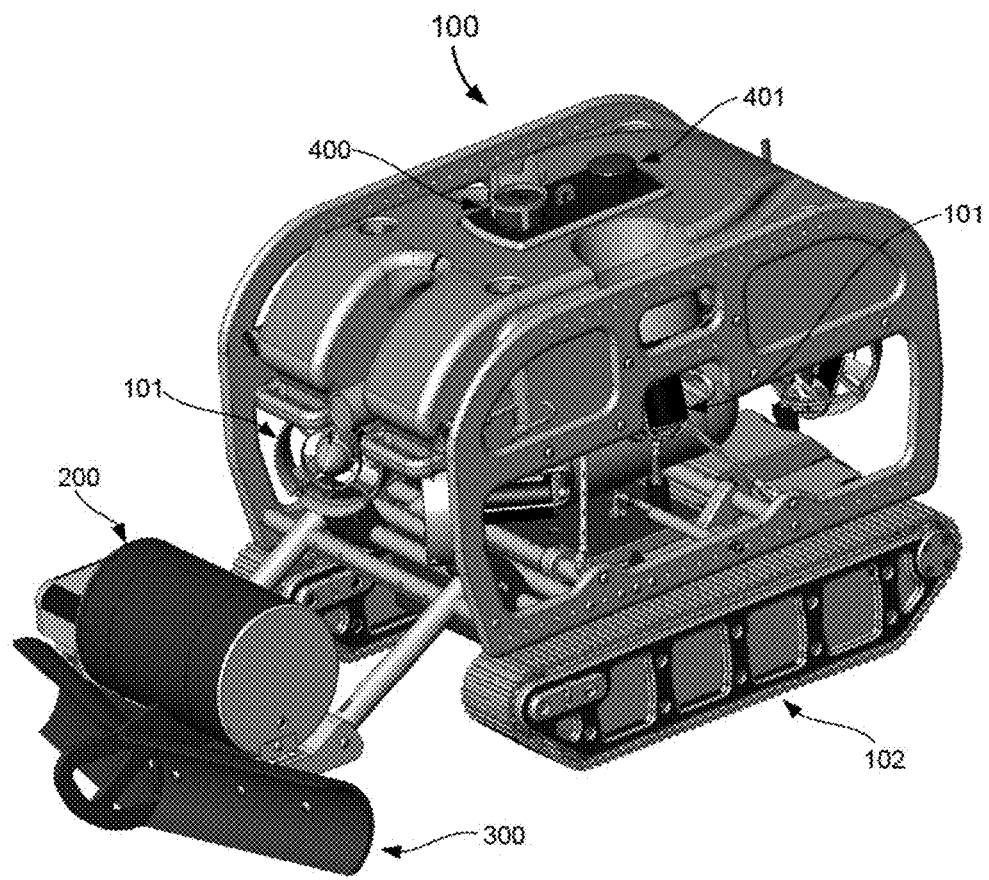
FIG. 2 is a perspective view of the ROV.
Figure 3:
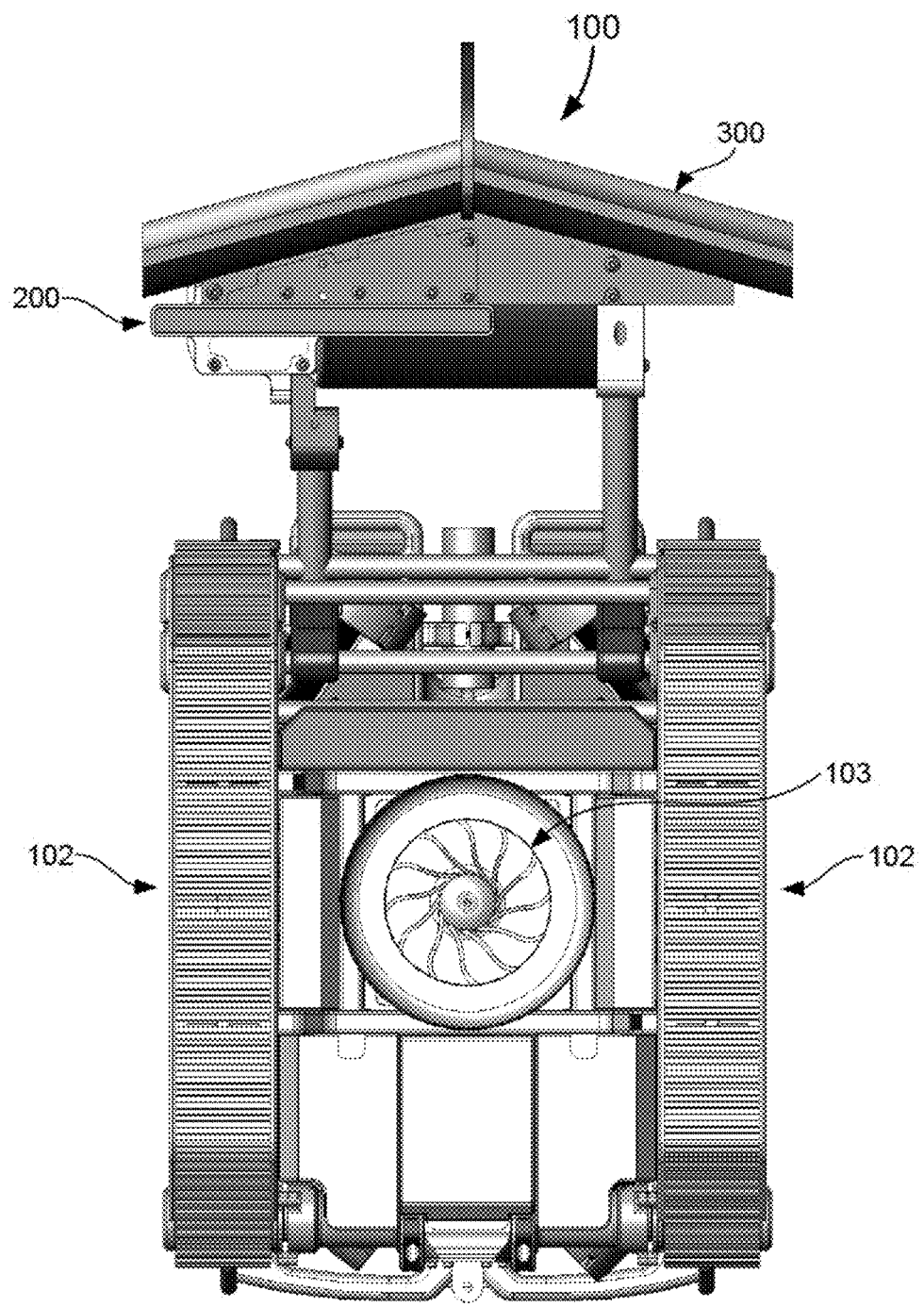
FIG. 3 is a bottom view of the ROV.
Figure 4:
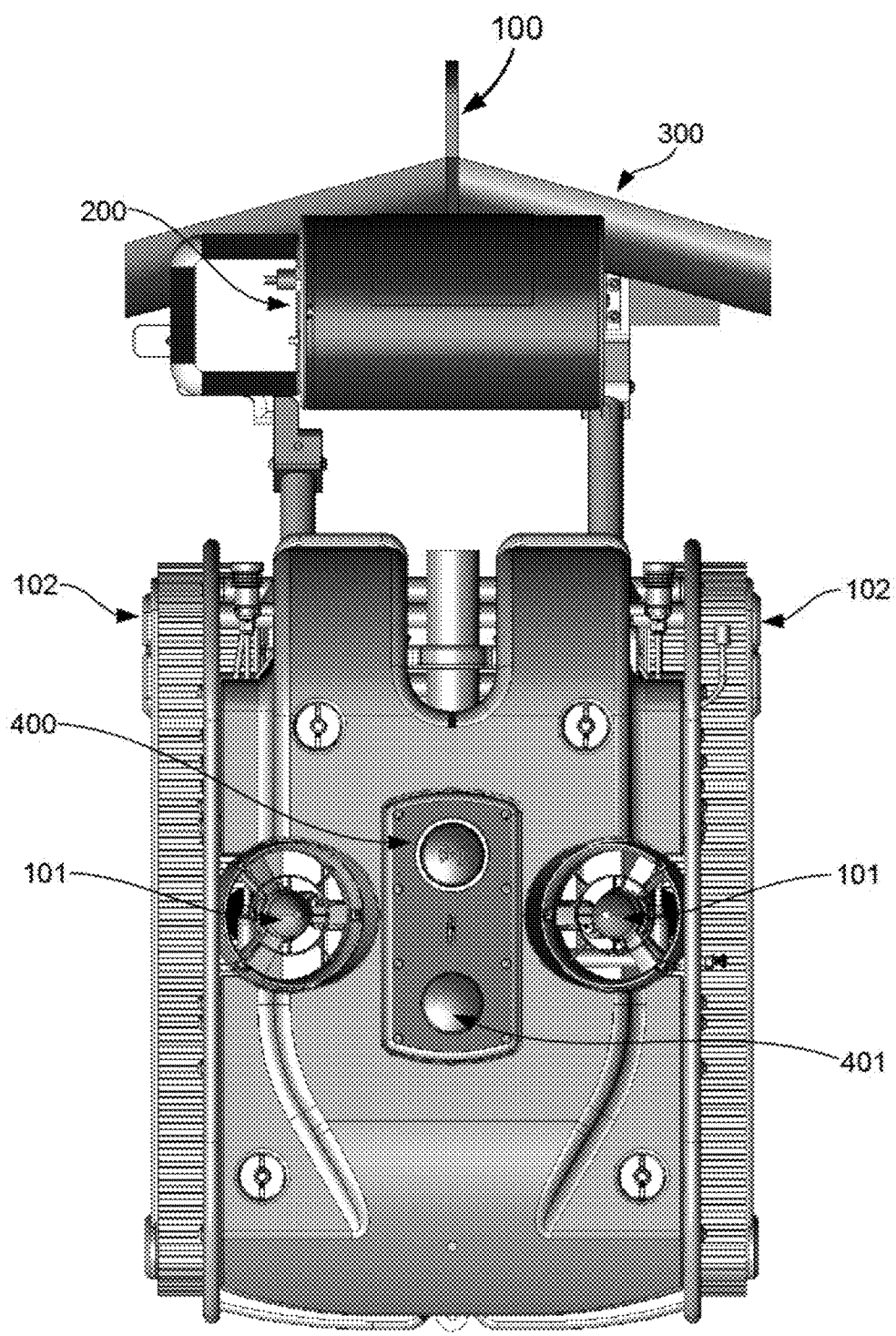
FIG. 4 is a top view of the ROV.
Figure 5:
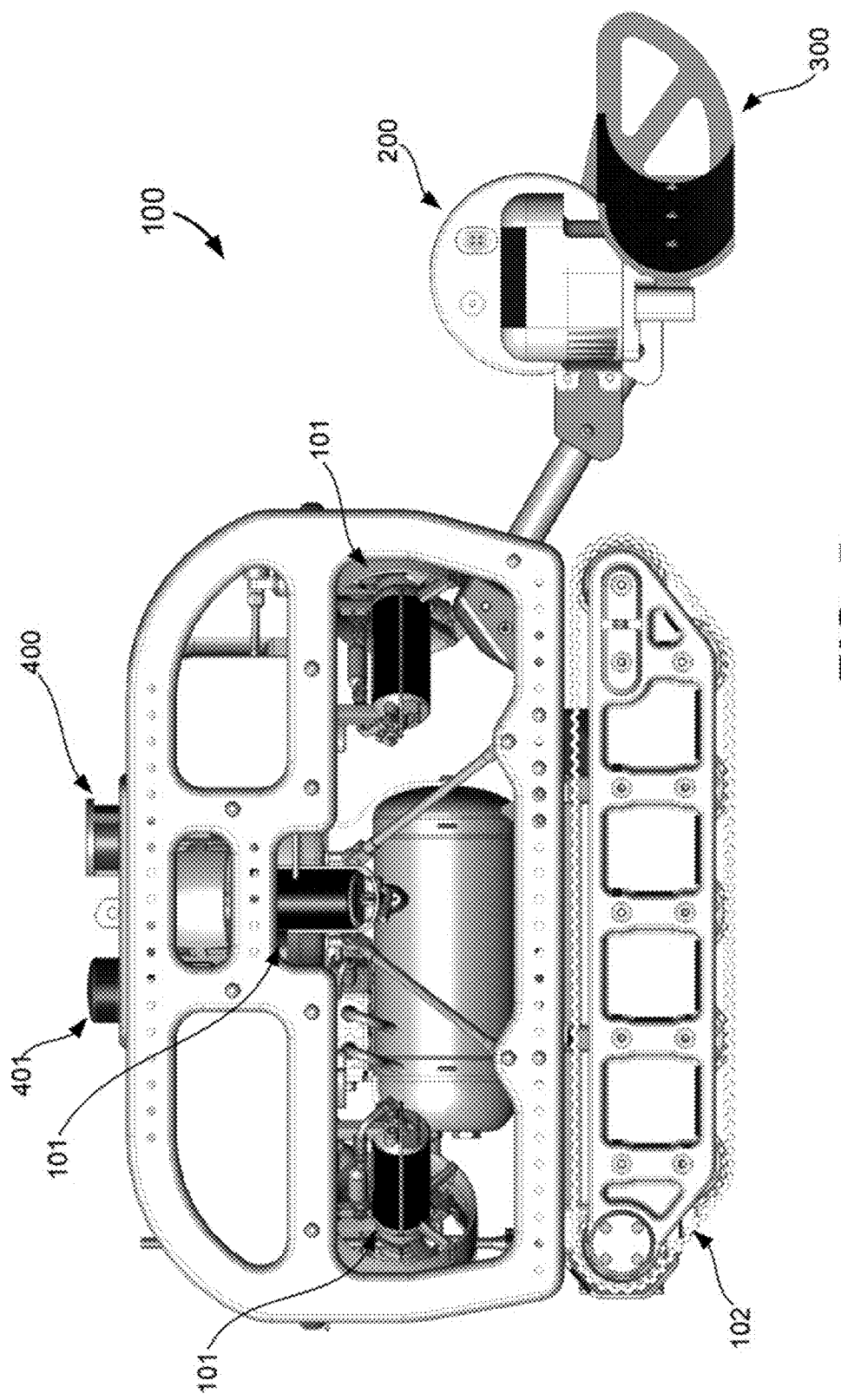
FIG. 5 is a sectional view of the ROV taken from A-A.
Figure 6:
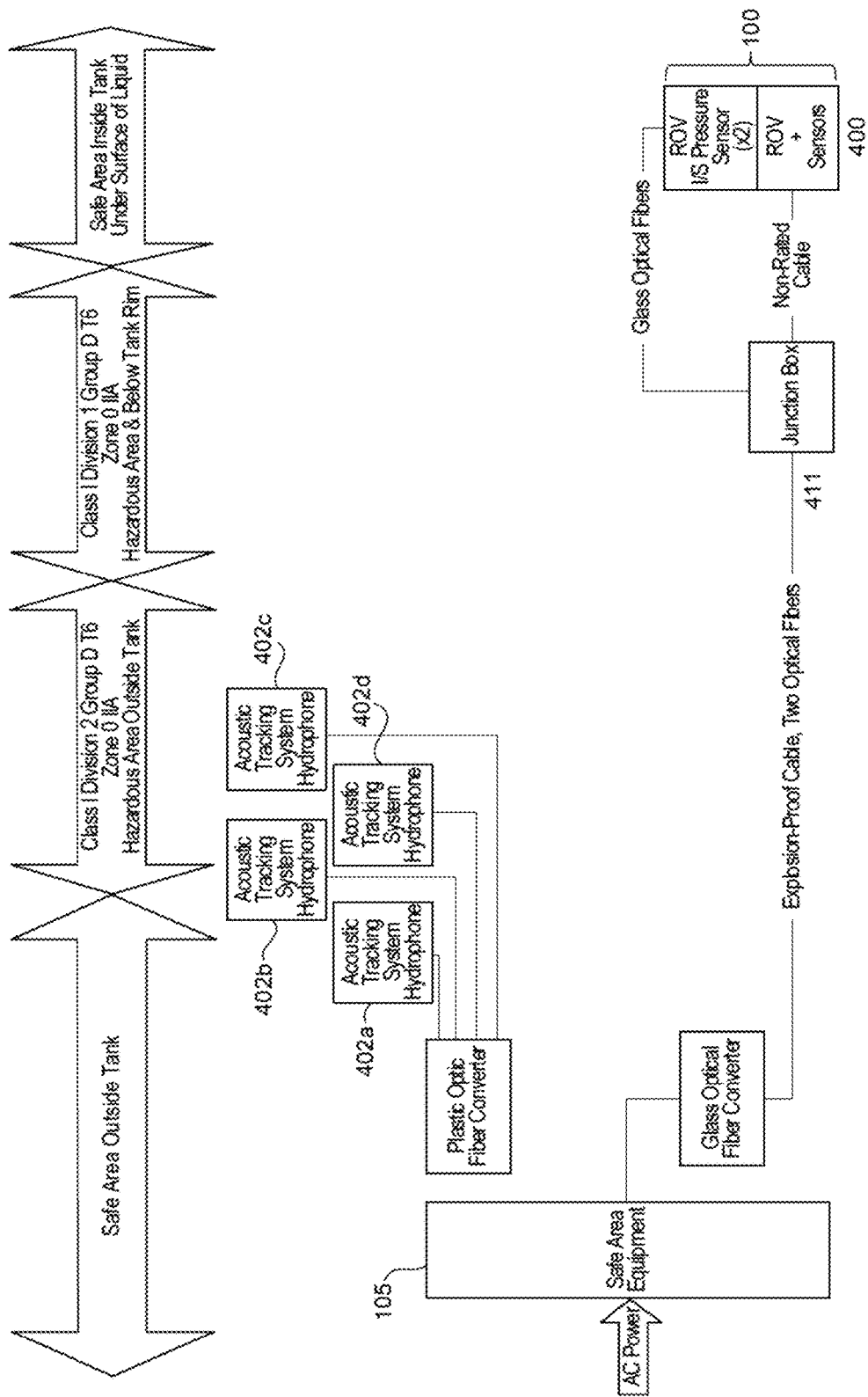
FIG. 6 is a schematic showing safe area operations.
Figure 6A:
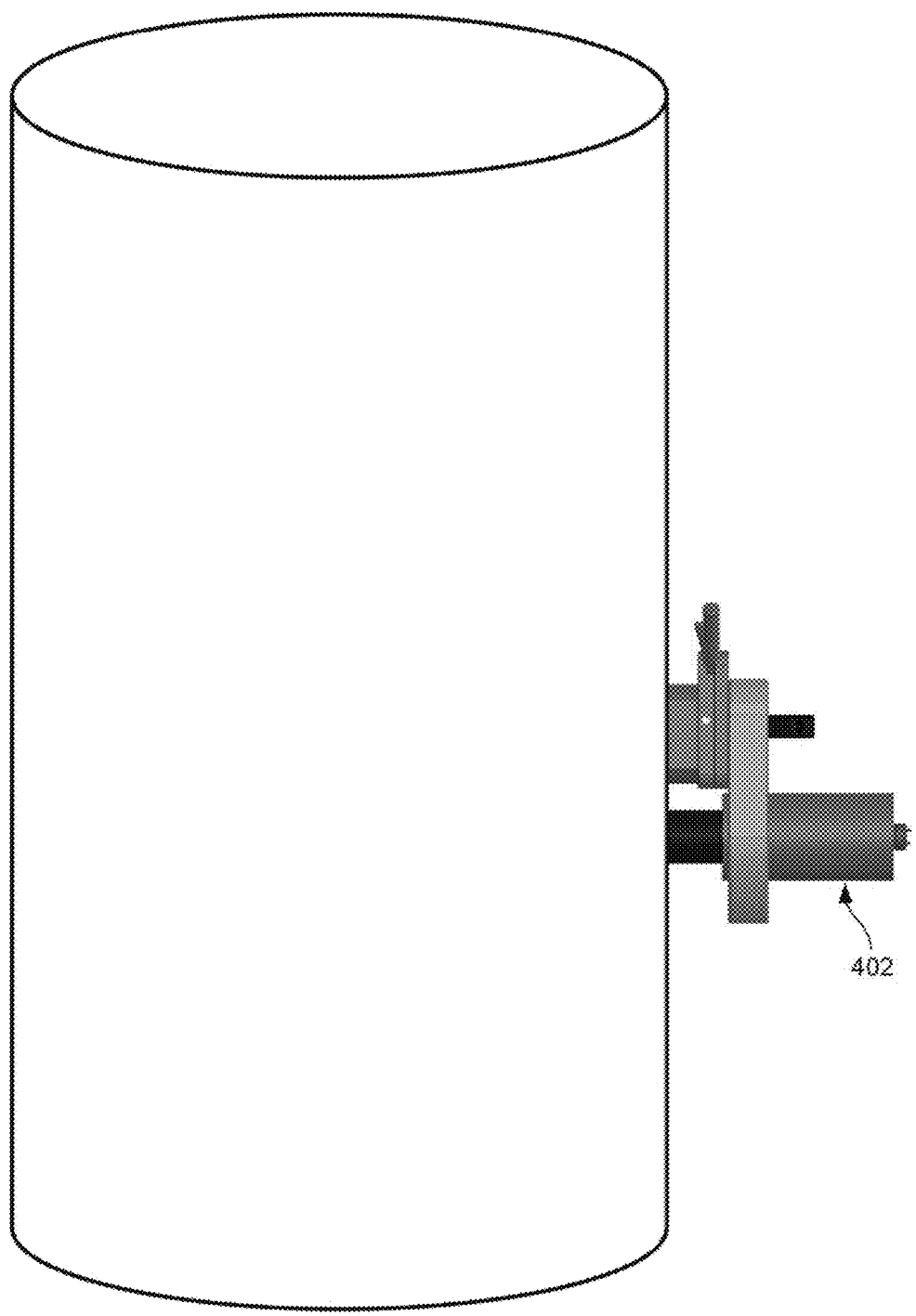
FIG. 6a is a side perspective view of an exemplary hydrophone base station.

In the following detailed description, reference is made to the accompanying drawings, which form a part hereof. In the drawings, the use of similar or the same symbols in different drawings typically indicates similar or identical items, unless context dictates otherwise.

The illustrative embodiments described in the detailed description, drawings, and claims are not meant to be limiting. Other embodiments may be utilized, and other changes may be made, without departing from the spirit or scope of the subject matter presented here.

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken as limiting.

The present application may use formal outline headings for clarity of presentation. However, it is to be understood that the outline headings are for presentation purposes, and that different types of subject matter may be discussed throughout the application (e.g., device(s)/structure(s) may be described under process(es)/operations heading(s) and/or process(es)/operations may be discussed under structure(s)/process(es) headings; and/or descriptions of single topics may span two or more topic headings). Hence, the use of the formal outline headings is not intended to be in any way limiting.

Referring to FIGS. 2-6, embodiments are provide for an automated tank surveyor ("ROV") (100) that mobilizes at least an ultrasound measurement system (200) and an acoustic tracking system (401) to survey tank walls and floor to detect corrosion, fissures, cracks, and other anomalies. The ROV (100), the ultrasound measurement system (200), and the acoustic tracking system (401) receive and transmit data to a telemetry system (105). The telemetry system (105) is any known automated communications process by which data is received and transmitted. The telemetry system (105) is positioned at a location outside a tank (10). In some embodiments the ROV (100) is further comprised of a plow (300) which may be used to displace sediment that may occlude sound path between the ultrasound measurement system (200) and the surface to be measured.

In some embodiments, the ROV (100) has six traditional underwater thrusters (101) used to generate five degrees of freedom motive force when swimming: surge (forward/reverse), sway (port/starboard), heave (vertical), roll (CW/CCW), and yaw (turn port or starboard). The ROV (100) moves in "flight mode" through liquid to a particular area of the tank to be surveyed, and then transitions into "crawler mode" for precise surface positioning using continuous tracks (102) and at least one vortex generator (103) (described in U.S. Pat. No. 6,881,025). This mobility system allows the ROV (100) to remain motionless, to crawl along vertical tank walls, or plow through sludge, for example. The ROV (100) is powered and controlled through an electronic communications cable (411) connected to a telemetry system (105).

In some embodiments, the ROV is further comprised of obstacle avoidance sonar (400). The obstacle avoidance sonar (400) may be passive or active and communicates with the telemetry system (105).

The acoustic tracking system (401) helps the ROV (100) avoid obstacles and navigate within the tank. The acoustic tracking system (401) is comprised of at least one pinger (403) and at least three hydrophone base stations (402) operably attached to the outside of a vessel (10) wall; preferably, the hydrophone base station (402) magnetically attaches. Preferably, the acoustic tracking system (401) is comprised of at least four hydrophone bases stations (402a, 402b, 402c, 402d). Preferably, the four hydrophone base stations (402a, 402b, 402c, 402d) are mounted on the North, East, South, and West sides of a tank at varying heights. To alleviate potential problems due to acoustic shielding by structures inside of the tank (e.g. ladders and pipes) more than four hydrophone base stations (402) may be used.

The pinger (403) and the hydrophone base station (402) have a common clock. Preferably, the clock has µs accuracy. To mark the location of the ROV (100) a simultaneous electronic timing pulse goes out to the pinger (403), signaling it to send out a pulse, and the hydrophone base stations (402), signaling each hydrophone base station (402) to start its clocks. As each hydrophone base station (402) receives a pulse from the pinger (403), the common clock is stopped. The 'time of flight' data from each hydrophone base station is passed to the telemetry system (105) where the data may be passed through any known triangulation algorithm in order to accurately locate the ROV (100).

Figure 7:
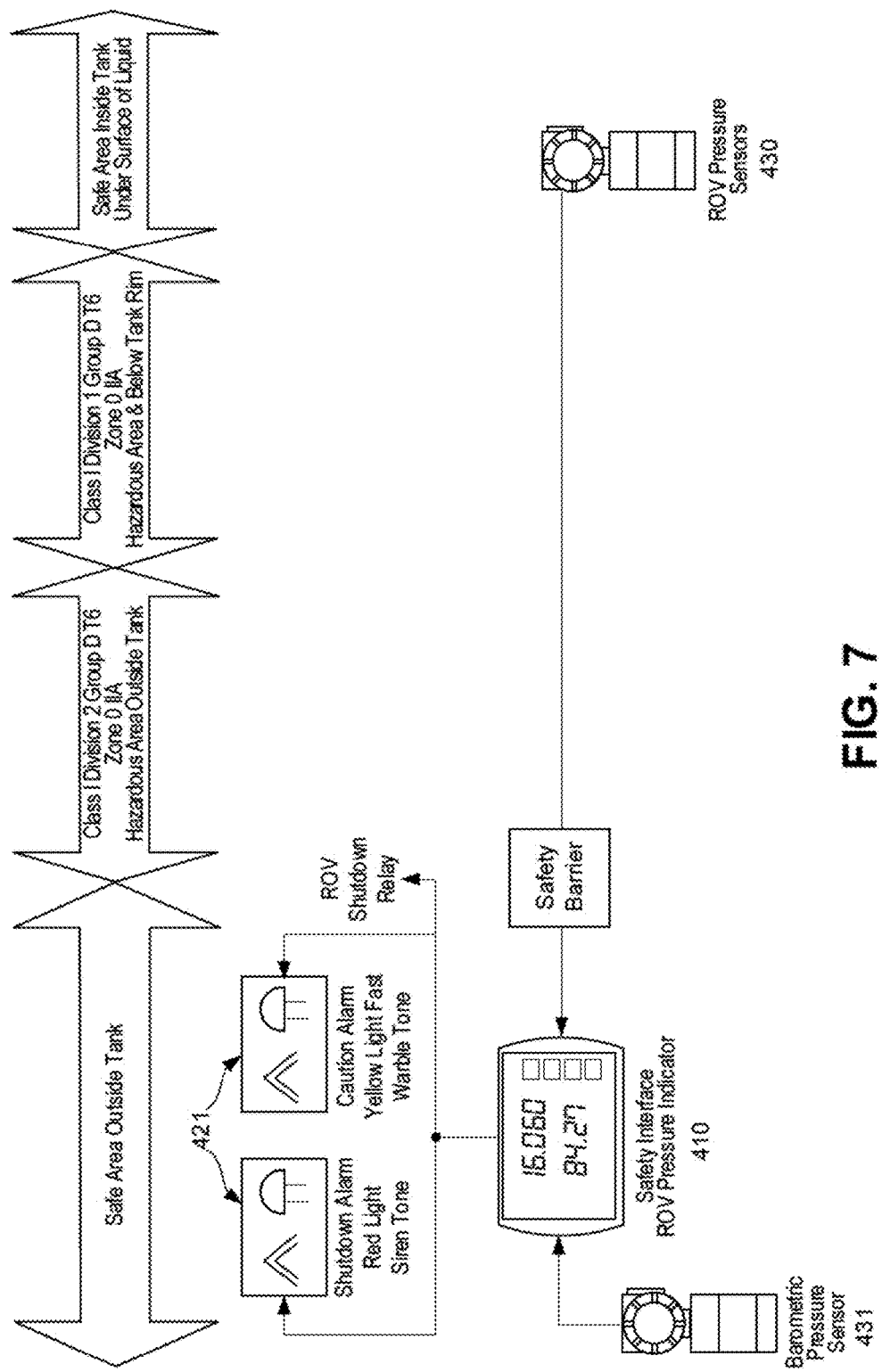
FIG. 7 is a schematic showing an exemplary safety interlock system.
Figure 8:
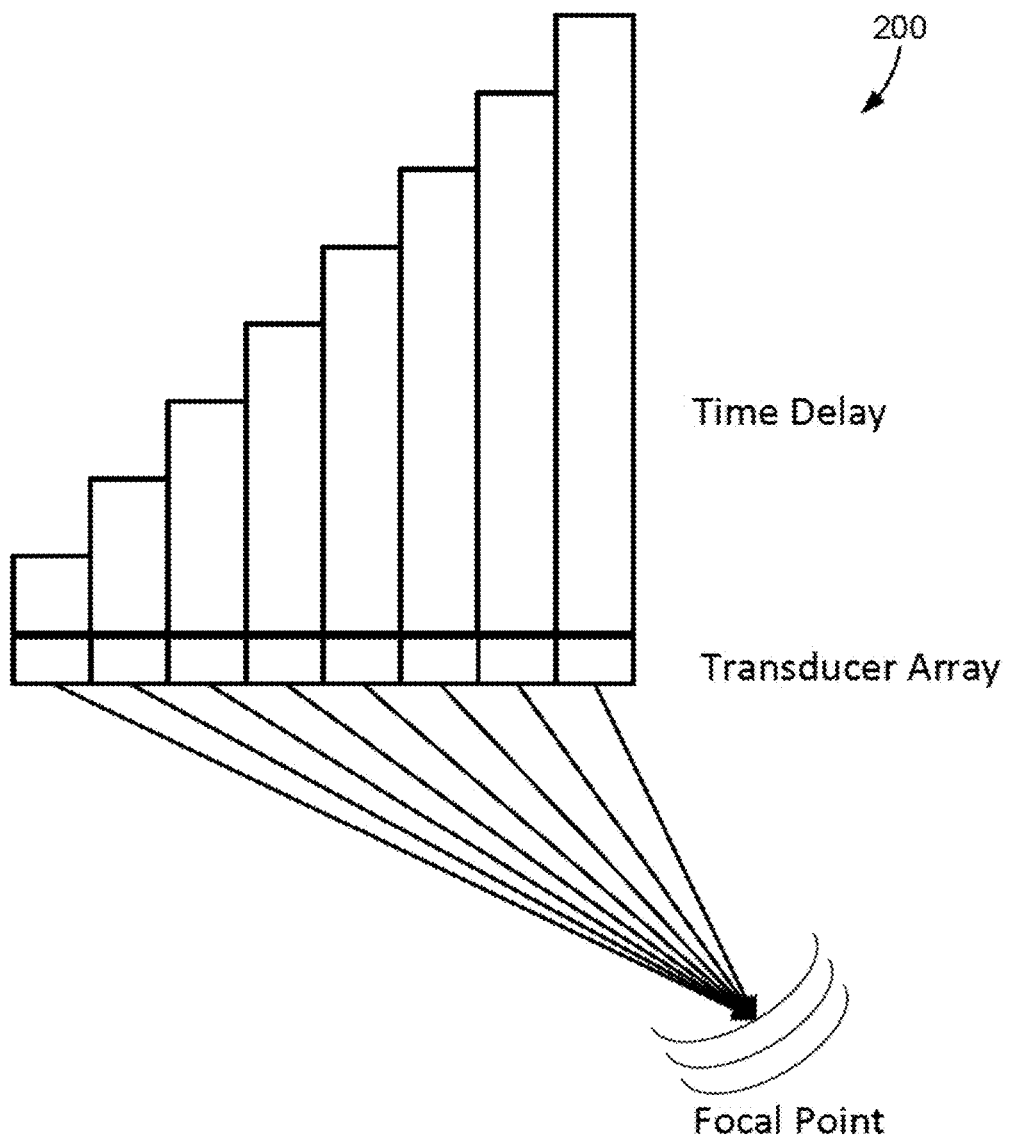
FIG. 8 is multi-beam type phased array schematic.
Figure 9A:
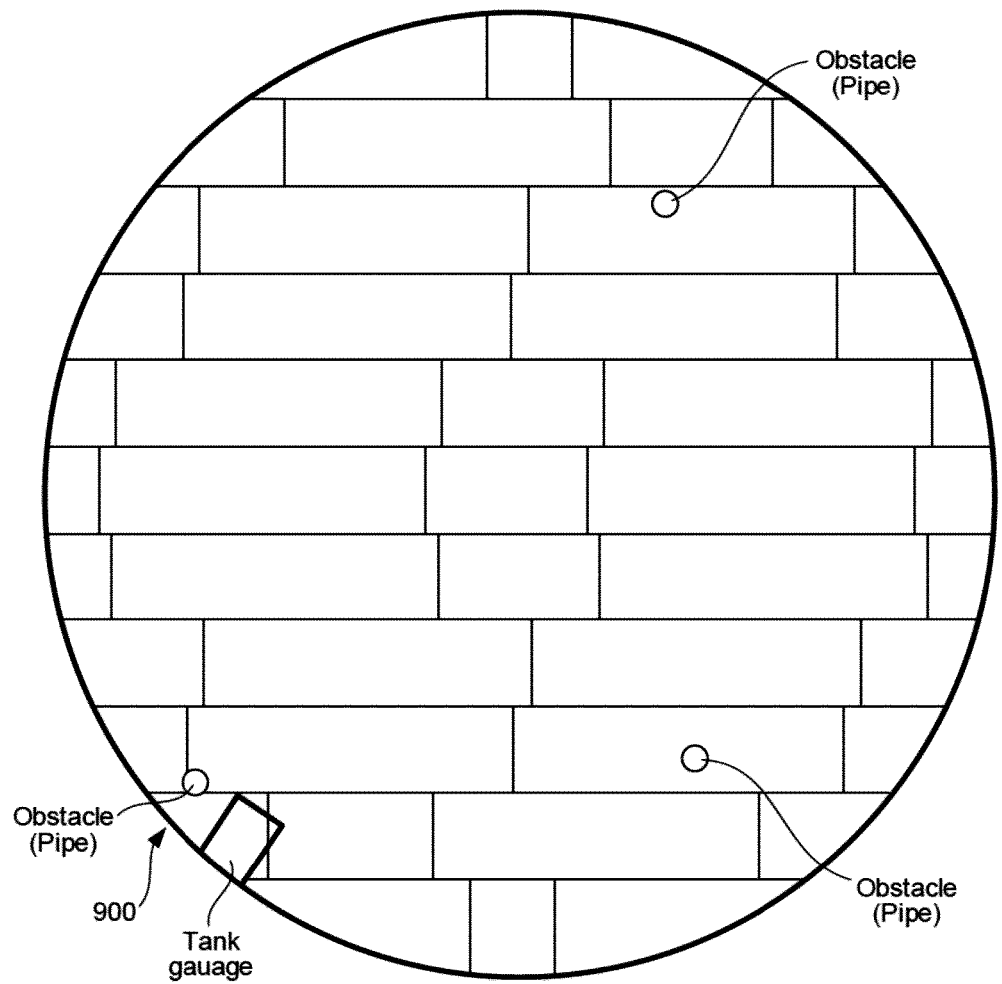
FIG. 9a is an exemplary schematic of an exemplary tank floor plan.
Figure 9B:
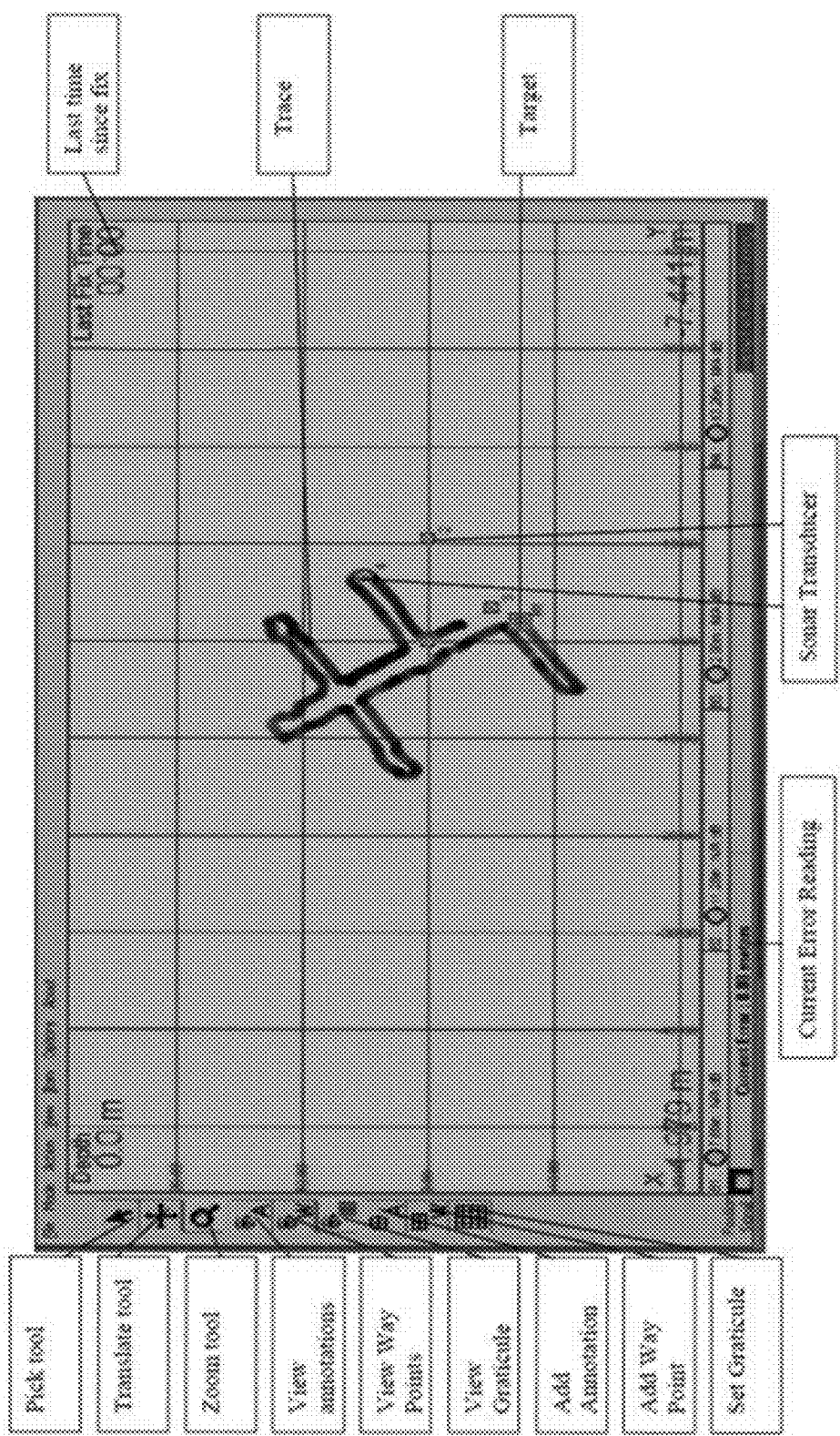
FIG. 9b is an exemplary schematic of ROV positioning.
Figure 9C:
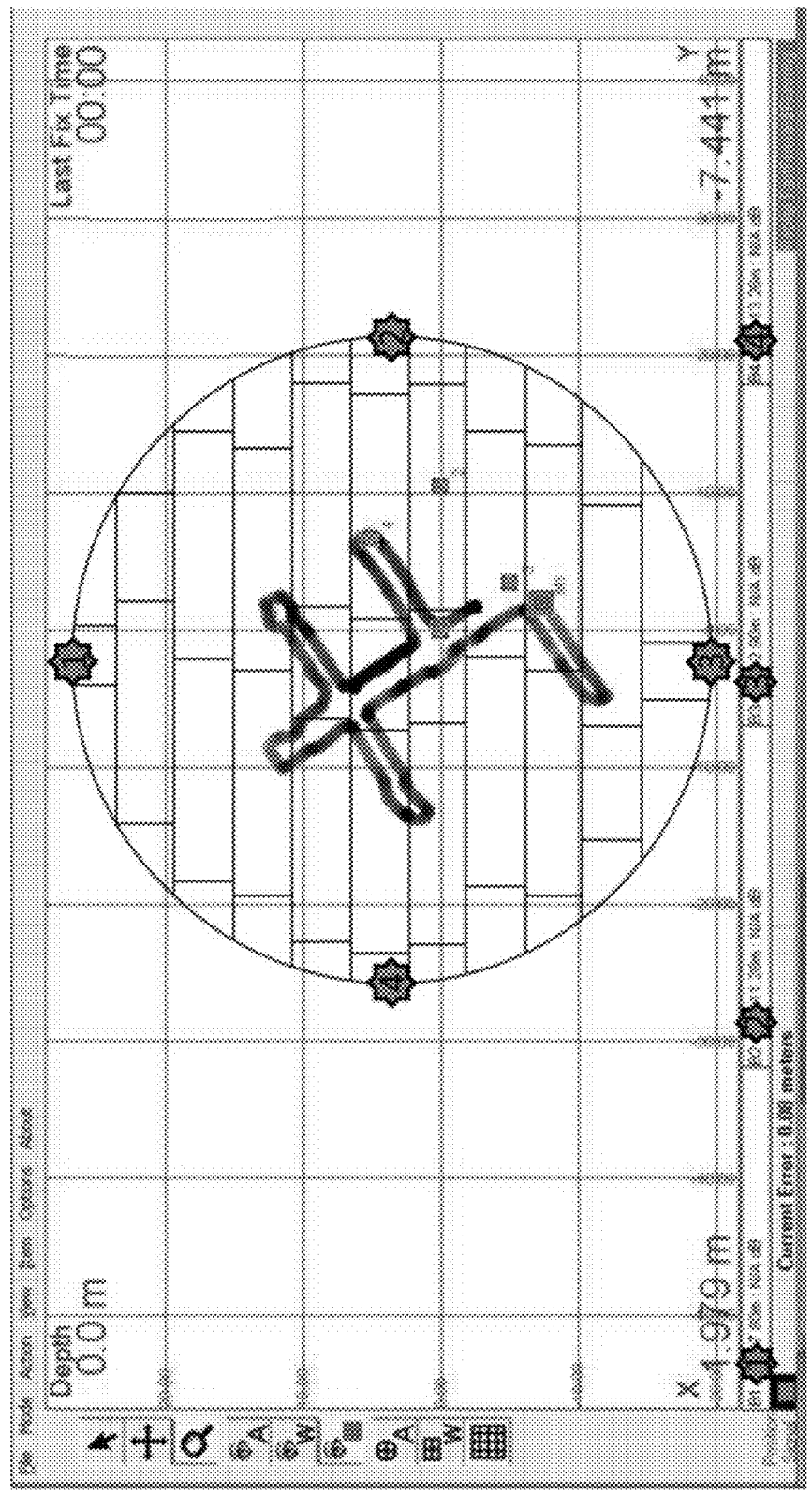
FIG. 9c is an exemplary schematic of ROV positioning superimposed on a tank floor plan.
Figure 9D:
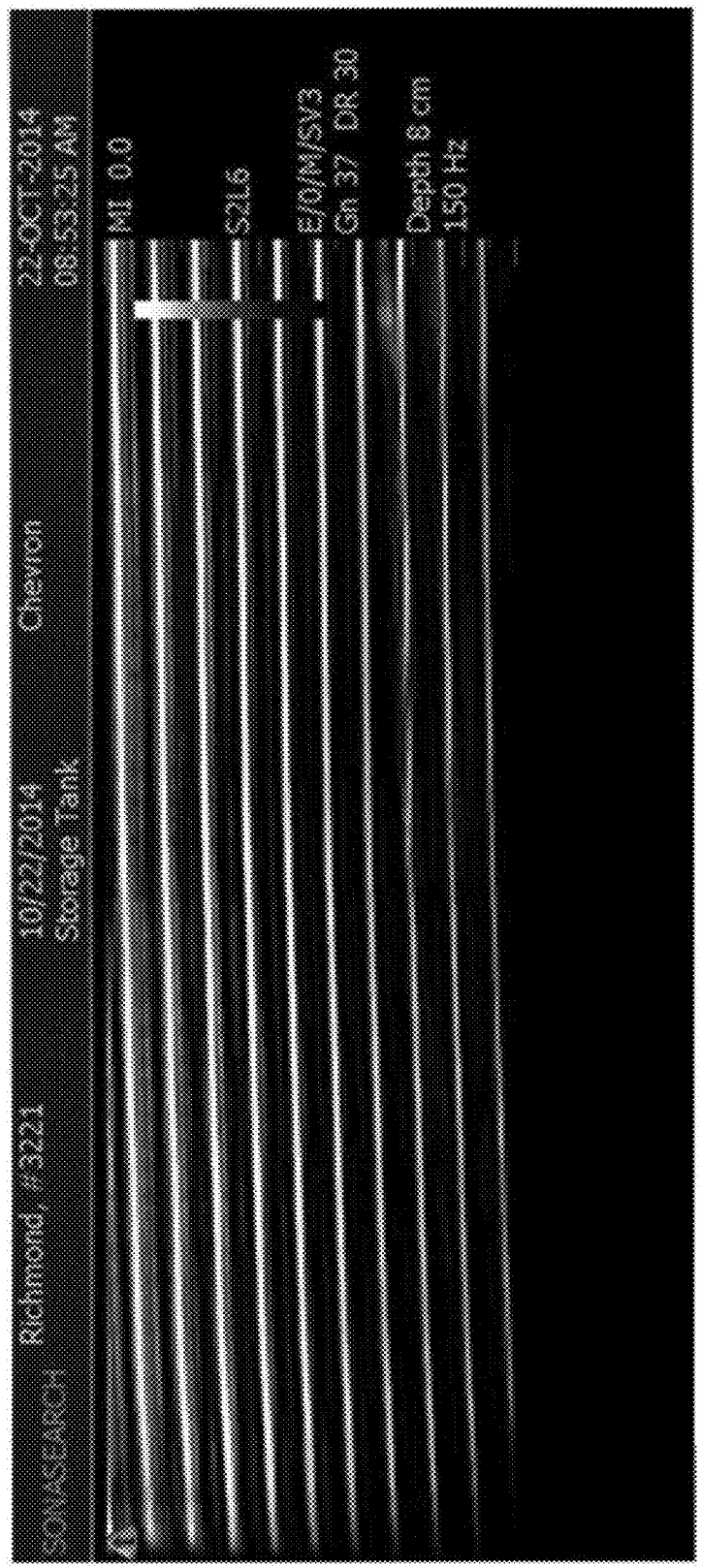
FIG. 9d is an exemplary schematic showing data from the multi-beam phased array.
Figure 9E:
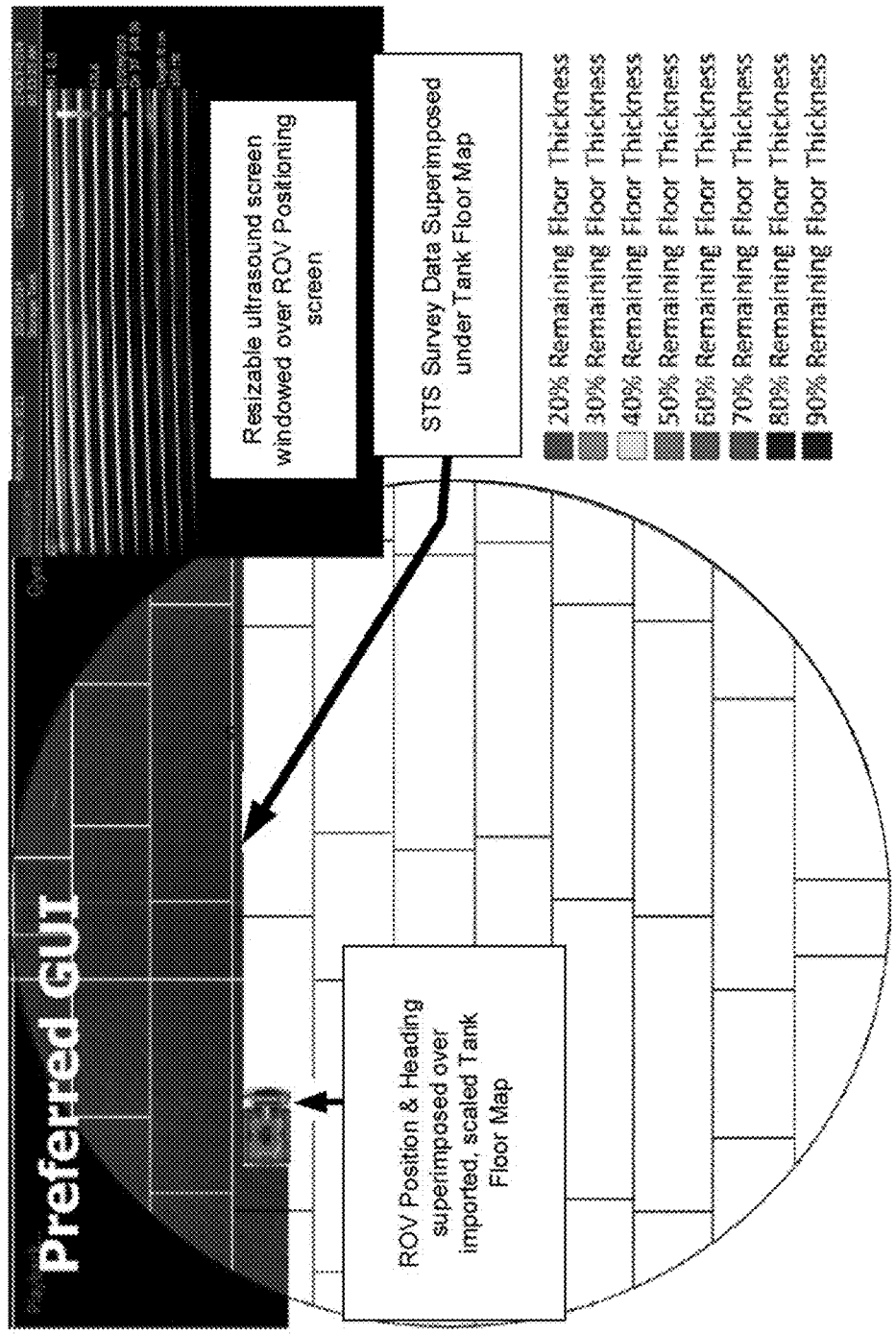
FIG. 9e is an exemplary schematic of survey data superimposed on a tank floor map.
Figure 9F:
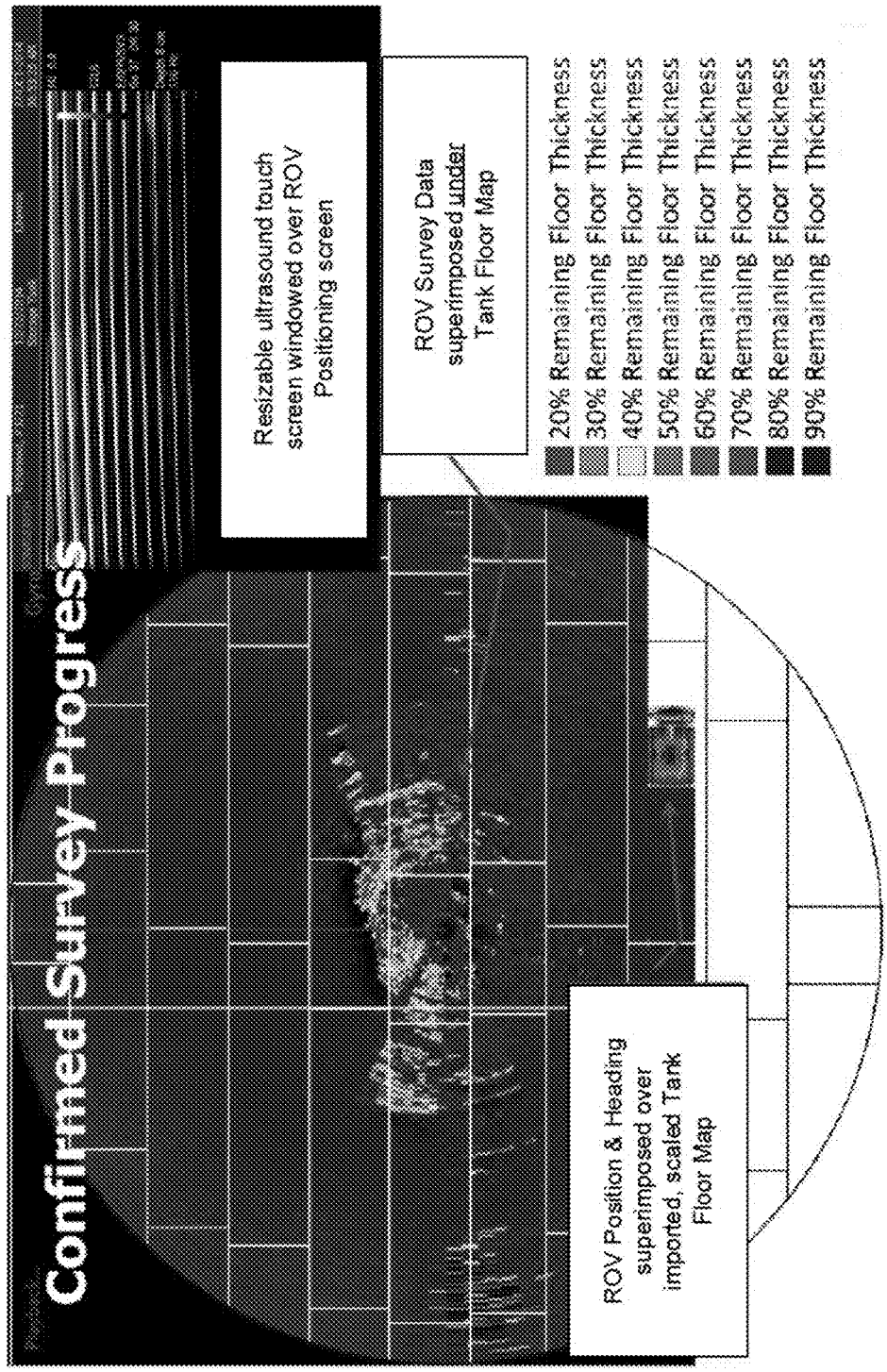
FIG. 9f is an exemplary schematic of a survey data superimposed on a tank floor map.
Figure 9G:
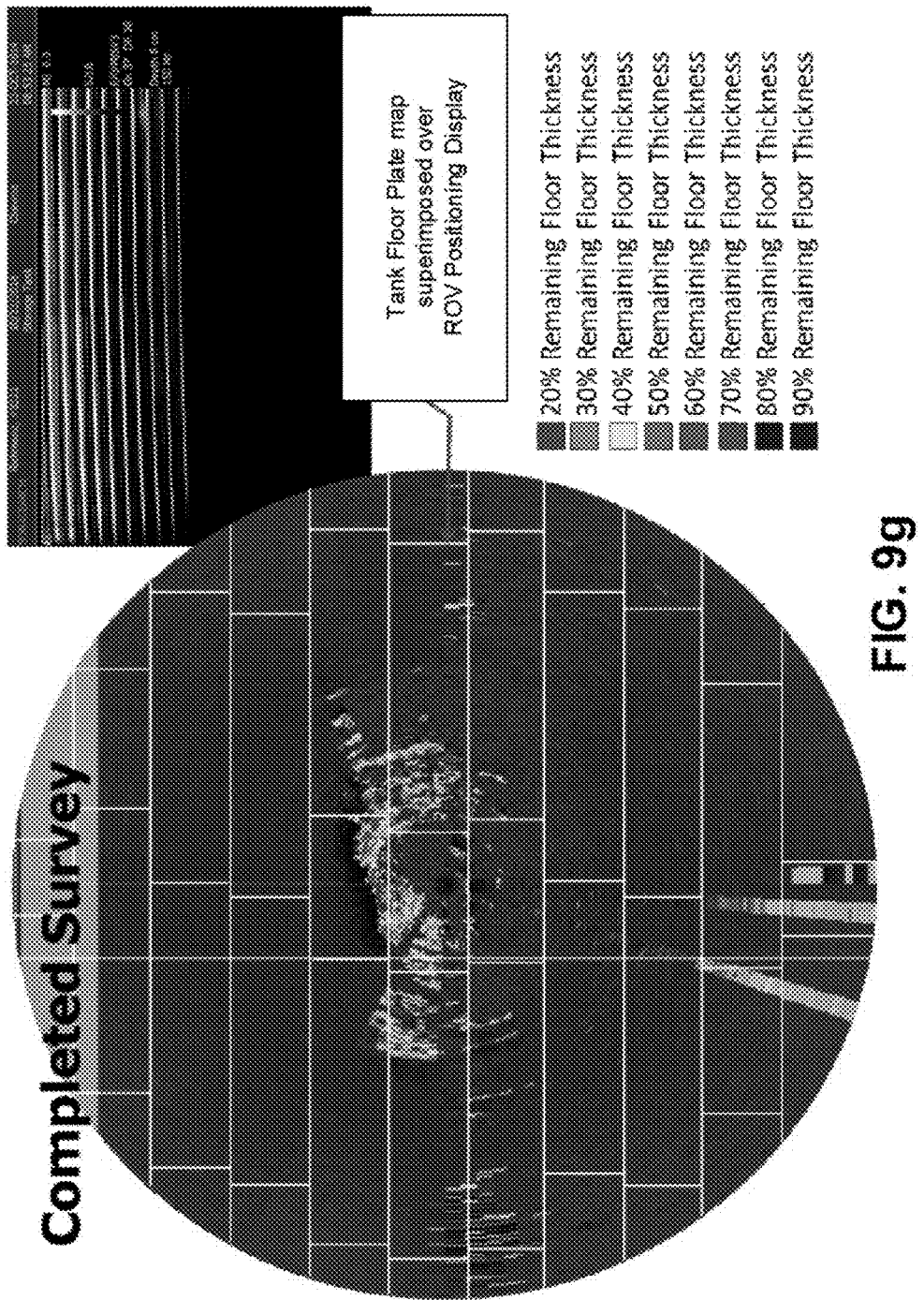
FIG. 9g is an exemplary completed survey map.

Referring to FIG. 7, in some embodiments, the ROV (100) has a safety interlock (410). The ROV (100) may be powered by high voltage. Because the ROV (100) must be able to move in liquid it cannot be made explosion proof or it would be too heavy to "swim". However, once the ROV (100) is below the surface of the liquid in a tank, it is no longer in a hazardous area. A safety lock (410) is used to ensure that the ROV (100) is never under power when in transition through hazardous areas. The ROV (100) can be powered up only when it is located a safe distance below the surface of the liquid in the tank.

The safety interlock (410) is comprised of two independent systems: an intrinsically safe pressure transmitter (430) and the acoustic tracking system (401). The intrinsically safe pressure transmitter (430) will continuously measure the ambient pressure at the top of the ROV (100); as the pressure increases the depth of the ROV (100) increases in the tank. The intrinsically safe pressure transmitter (430) measures the sum of the weight of the fluid column and the ambient atmospheric pressure; ambient pressure can vary greatly over time. Consequently, a barometric pressure transmitter (431), located in the safe area, will continuously monitor ambient atmospheric pressure. The difference between the barometric pressure transmitter (431) and the intrinsically safe pressure transmitter (430) can be used to more accurately measure the depth of the ROV (100), confirming it is below the ROV exclusion zone.

Preferably, a custom EX rated umbilical cable (411) will connect from the telemetry system (105) in the safe area to the ROV (100). Inside the umbilical cable (411), a separated jacketed and screened twisted pair of wires is used for the safety interlock (410). The remaining conductors and optical fibers in the umbilical cable (411) provide a pathway for electrical power, ROV (100) control and sensor data. Preferably, the umbilical cable (411) is jacketed with a material that is compatible with the fluids in the tank and flexible enough to allow the ROV (100) to have free movement. Preferably, the umbilical cable (411) is negatively buoyant and will sink to the bottom of a tank filled with liquid.

To ensure the ROV (100) is safely isolated from the hazardous area during operation, an ROV exclusion zone (420) extends from the surface of the liquid in the tank down to a predetermined depth. The ROV (100) can only be powered up when it is in the fluid below the ROV exclusion zone (420). If during deployment or during operation, the ROV (100) approaches the ROV exclusion zone (420), the operator will be warned with at least and audible and/or visual alarm (421). If the ROV (100) enters the ROV exclusion zone (420), the system will be immediately and automatically powered down, and distinctly different audio/visual alarms (442) will identify the reason for shut down.

Referring to FIGS. 1-6, 8, preferably, the ultrasound measurement system (200) is a multi-beam type phased array. The phased array ultrasound measurement system (200) is comprised of a plurality of ultrasonic transducers, each of which can be pulsed independently. By varying the timing of each transducer to pulse one by one along a row, a pattern of constructive interference results in a beam at a set angle. In other words, the beam can be steered electronically. Preferably, the beam profile has less than 2 dB drop between transducers allowing a very high density of energy in the tank floor improving performance. The beam type phased array system (200) may be steered in pattern format to examine tank walls and floor. In some embodiments, depending on tank size or suspected anomalies, more than one beam type phased array system (200) may be used.

Steering the beam typed phased array system (200) allows the tank inspector to utilize a defined search pattern so that anomalies of varying types are found and accurately defined.

The search pattern of the ROV (100) is dependent on the characteristics of the environment to be inspected. Exemplary search patterns include increasing concentric circles, decreasing concentric circles, grid pattern, plate by plate amongst others regardless of the inspection pattern selected, the ROV (100) provides near continuous inspection of a tank. The frequency with which samples are taken is determined by ultrasound pulse repetition frequency and the speed of the ROV (100). Range resolution (Δr) is a function of ultra sound frequency (f), the sound velocity in the media being tested (cΔt) and the number of pulses (Δt):

$$\Delta r = c\Delta t/f * \Delta t/2.$$

The ROV (100) typically uses a single pulse for each transmit cycle, so Δt=1.

For example, assuming a single pulse at an ultra sound frequency of 6.2 Mhz in water (1500 m/s), the range resolution would be 121 μm (0.0048"). Given a 10" linear array, the lateral resolution would be similar, with a vertical resolution of half the lateral resolution.

Referring to FIGS. 9a-9g, the telemetry system (105) compiles the data received by the ultrasound measurement system (200) and the acoustic tracking system (401) to measure anomalies in the tank. The telemetry system time-stamps, sample-frame by sample-frame, data collect in each frame from the ultrasound measurement system (200) and the acoustic tracking system (401). Correlating the time-stamps of each set of data provides a direct, 3D position fix of where each ultrasound sample was taken and whether anomalies were found. In one embodiment, a tank floor map (900) is loaded into the telemetry system (105) prior to survey of a tank (10). The tank floor map (900) describes, at a minimum, tank identification, tank location, tank size, position and original, as installed thickness of each floor plate, and any obstacles (e.g. sumps, pipes). The correlated data may be overlaid on an imported tank map assembling a survey report.

What is claimed is:

1. A remotely operated vehicle ("ROV") system configured to non-destructively inspect the integrity of an interior of a vessel, the system comprising:
    an ROV comprising an ultrasound phased array comprised of a plurality of ultrasound transducers, tracks configured to assist the ROV to crawl on an inner surface of the vessel, and a plurality of thrusters configured to assist the ROV to swim through a liquid contained within the vessel;
    an acoustic tracking system configured to track the location of the ROV in the vessel; and
    a telemetry system configured to receive and compile data from the ultrasound phased array and the acoustic tracking system, wherein the telemetry system is pre-loaded with a template of the interior of the vessel, including positions of floor plates and any obstacles.

2. The ROV system of claim 1, wherein the ultrasound phased array is configured to measure both a floor and a wall of the vessel from a single position of the ROV.

3. The ROV system of claim 1, further comprising a plurality of ultrasound phased arrays.

4. The ROV system of claim 1, wherein the acoustic tracking system comprises at least one pinger and at least three hydrophone base stations.

5. The ROV system of claim 4, wherein the at least three hydrophone base stations are disposed on an outside of the vessel.

6. The ROV system of claim 1, further comprising a safety interlock comprising a pressure transmitter configured to continuously measure ambient pressure at the top of the ROV.

7. The ROV system of claim 6, wherein the safety interlock is configured to prevent the ROV, when descending into the vessel, from being powered until it is below a pre-determined exclusion zone.

8. The ROV system of claim 6, wherein the safety interlock is configured to prevent the ROV, when ascending from the bottom of the vessel, from being powered when it reaches a pre-determined exclusion zone.

9. The ROV system of claim 6, wherein the safety interlock further comprises a barometric pressure transmitter, located outside the vessel, that is configured to continuously measure ambient atmospheric pressure, and wherein the safety interlock is configured to accurately measure the depth of the ROV by taking into account the ambient atmospheric pressure.

10. The ROV system of claim 1, wherein the ultrasound phased array is a linear ultrasound phased array.

11. The ROV system of claim 1, wherein the telemetry system is configured to time-stamp data generated by the ultrasound phased array and data generated the acoustic tracking system and correlate the data generated by the ultrasound phased array and with a position on the vessel.

12. The ROV system of claim 1, wherein the obstacles are selected from the group consisting of sumps, pipes, and a combination thereof.

13. A method of non-destructively inspecting the integrity of an interior of a vessel using an ROV system according to claim 1, the method comprising:
    providing an ROV in an interior of the vessel while tracking a location of the ROV in the vessel using an acoustic tracking system;
    positioning the ROV at a measurement location in the vessel by moving the ROV by crawling on the interior surface of the vessel or swimming through a liquid contained in the vessel;
    inspecting the measurement location using an ultrasound phased array attached to the ROV and transmitting data generated to a telemetry exterior to the vessel; and
    in the telemetry system, compiling data from the ultrasound phased array and the acoustic tracking system to provide a measurement of the measurement location, wherein the telemetry system is pre-loaded with a template of the interior of the vessel, including positions of floor plates and any obstacles.

14. The method of claim 13, wherein positioning the ROV includes maneuvering the ROV around obstacles defined on the template.

15. The method of claim 13, wherein inspecting the measurement location includes using the ultrasound phased array to measure both a floor and a wall of the vessel from a single position of the ROV.

16. The method of claim 13, wherein the ROV system further comprises a safety interlock system and the method further includes a step of preventing the ROV, when descending into the vessel, from being powered until it is below a pre-determined exclusion zone.

17. The method of claim 13, wherein the ROV system further comprises a safety interlock system and the method further includes a step of preventing the ROV, when ascending from the bottom of the vessel, from being powered when it reaches a pre-determined exclusion zone.

18. The method of claim 13, wherein the telemetry system is configured to time-stamp data generated by the ultrasound phased array and data generated the acoustic tracking system and correlate the data generated by the ultrasound phased array and with a position on the vessel.

\* \* \* \* \*